US 6,624,319 B2

(12) United States Patent
Hofen et al.

(10) Patent No.: US 6,624,319 B2
(45) Date of Patent: Sep. 23, 2003

(54) PROCESS FOR THE EPOXIDATION OF OLEFINS

(75) Inventors: Willi Hofen, Rodenbach (DE); Georg Thiele, Hanau (DE)

(73) Assignees: Degussa AG, Düsseldorf (DE); Uhde GmbH, Dortmund (DE)

( * ) Notice: Subject to any disclaimer, the term of this patent is extended or adjusted under 35 U.S.C. 154(b) by 0 days.

(21) Appl. No.: 10/203,185

(22) PCT Filed: Feb. 2, 2001

(86) PCT No.: PCT/EP01/01110
§ 371 (c)(1),
(2), (4) Date: Oct. 4, 2002

(87) PCT Pub. No.: WO01/57009
PCT Pub. Date: Aug. 9, 2001

(65) Prior Publication Data
US 2003/0109725 A1 Jun. 12, 2003

(30) Foreign Application Priority Data
Feb. 7, 2000 (EP) ............................................. 00102542

(51) Int. Cl.$^7$ ............................................. C07D 301/32
(52) U.S. Cl. ........................................ 549/541; 549/531
(58) Field of Search ................................. 549/541, 531

(56) References Cited

U.S. PATENT DOCUMENTS

| 2,870,171 | A | 1/1959 | Gable |
| 4,410,501 | A | 10/1983 | Taramasso et al. |
| 4,833,260 | A | 5/1989 | Neri et al. |
| 5,523,426 | A | 6/1996 | Jubin, Jr. et al. |
| 5,591,875 | A | 1/1997 | Chang et al. |
| 5,599,955 | A | 2/1997 | Vora et al. |
| 5,620,935 | A | 4/1997 | Thiele |
| 5,675,026 | A | 10/1997 | Thiele |
| 5,760,253 | A | 6/1998 | Danner et al. |
| 5,849,937 | A | 12/1998 | Jubin, Jr. et al. |
| 5,849,938 | A | 12/1998 | Reuter et al. |
| 5,912,367 | A | 6/1999 | Chang |
| 6,042,807 | A | 3/2000 | Faraj |
| 6,063,941 | A | 5/2000 | Gilbeau |
| 6,372,924 | B2 | 4/2002 | Thiele |

FOREIGN PATENT DOCUMENTS

| DE | 196 23 611 | 12/1997 |
| DE | 197 23 950 | 12/1998 |
| DE | 197 54 185 | 2/1999 |
| DE | 198 35 907 | 2/2000 |
| EP | 0 106 671 | 4/1964 |
| EP | 0 100 118 | 2/1984 |
| EP | 0 100 119 | 2/1984 |
| EP | 0 757 045 | 2/1987 |
| EP | 0 230 349 | 7/1987 |
| EP | 0 230 949 | 8/1987 |
| EP | 0 568 336 | 11/1993 |
| EP | 0 568 337 | 11/1993 |
| EP | 0 583 828 | 2/1994 |
| EP | 0 645 473 | 3/1995 |
| EP | 0 659 473 | 6/1995 |
| EP | 0 712 852 | 5/1996 |
| EP | 0 719 768 | 7/1996 |
| EP | 0 795 537 | 2/1997 |
| EP | 0 827 765 | 8/1997 |
| EP | 0 930 308 | 7/1999 |
| EP | 0 936 219 | 8/1999 |
| EP | 1 066 711 | 12/1999 |
| EP | 1 122 248 | 8/2001 |
| EP | 1 138 387 | 10/2001 |
| EP | 1 221 442 | 7/2002 |
| JP | 2166636 | 6/1990 |
| JP | WO 00/17178 | 3/2000 |
| WO | WO 97/47613 | 12/1997 |
| WO | WO 97/47614 | 12/1997 |
| WO | WO 99/01445 | 1/1999 |
| WO | WO 99/07690 | 2/1999 |
| WO | 99/11639 | 3/1999 |
| WO | WO 00/07695 | 2/2000 |

*Primary Examiner*—Ba K. Trinh
(74) *Attorney, Agent, or Firm*—Smith, Gambrell & Russell, LLP

(57) ABSTRACT

The present invention relates to a process for the catalytic epoxidation of olefins in which in one reaction stage the olefin is reacted with aqueous hydrogen peroxide in an organic, water-miscible solvent in the presence of a titanium silicalite catalyst, wherein an exit gas stream is obtained which contains olefin oxide, unreacted olefin and oxygen and this exit gas stream is brought into contact in an absorption unit with the same solvent as used in the reaction stage and a solvent stream loaded with olefin and olefin oxide is drawn off from the absorption unit and an exit gas stream containing oxygen is discharged.

10 Claims, 2 Drawing Sheets

PROCESS FOR THE EPOXIDATION OF OLEFINS

This application is a 371 of PCT/EP 01/01110 filed Feb. 2, 2001.

The present invention relates to a process for the epoxidation of olefins, in which the exit gas stream leaving the reactor is further worked up.

PRIOR ART

It is known from EP A 100 118 that propene may be reacted with hydrogen peroxide to yield propene oxide if titanium silicalite is used as the catalyst. A secondary reaction which always occurs to a slight extent on the titanium silicalite catalyst is the decomposition of hydrogen peroxide to form molecular oxygen. If it is to be possible to operate the epoxidation process safely on an industrial scale, the oxygen formed must be removed from the reaction system. This is most simply achieved by discharging it with a propene exit gas stream. Such a process is known from EP A 659 473. The process does, however, have the disadvantage that considerable quantities of propene and propene oxide are lost together with the oxygen.

The object of the present invention is accordingly to provide a process for the epoxidation of olefins with which higher product yields may be achieved.

SUBJECT MATTER OF THE INVENTION

This object is achieved by a process for the catalytic epoxidation of olefins in which in one reaction stage the olefin is reacted with aqueous hydrogen peroxide in an organic, water-miscible solvent in the presence of a titanium silicalite catalyst, wherein an exit gas stream is obtained which contains olefin oxide, unreacted olefin and oxygen and this exit gas stream is brought into contact in an absorption unit with the same solvent as used in the reaction stage and a solvent stream loaded with olefin and olefin oxide is drawn off from the absorption unit and an exit gas stream containing oxygen is discharged.

DESCRIPTION OF THE INVENTION

It has now been found that the losses of olefin and olefin oxide which occur on discharge of the exit gas stream containing oxygen during the epoxidation of olefin with hydrogen peroxide and a titanium silicalite catalyst may be reduced in a simple manner by absorbing the majority of the olefin oxide, olefin and optionally the corresponding alkane with the solvent used for the epoxidation, discharging the oxygen and either returning the solvent stream loaded with olefin oxide and olefin to the reaction stage or passing it to a working up stage downstream from the reaction stage.

In a preferred embodiment, an inert gas stream is additionally introduced into the absorption unit, wherein the inert gas leaves the absorption unit together with the oxygen in the exit gas stream. The quantity of inert gas introduced is here preferably selected as a function of the quantity and composition of the exit gas stream leaving the reaction stage such that the exit gas stream leaving the absorption unit is no longer of an ignitable composition. This embodiment has the advantage that, even in the case of variation in product streams in the overall process, it is very simple constantly to maintain the composition of the gas phase in the absorption unit such that an ignitable mixture cannot occur within the absorption unit, nor may it leave said unit as an exit gas stream.

Suitable inert gases are any gases which dissolve only slightly in the solvent used for epoxidation, do not react with hydrogen peroxide and olefin oxide under the epoxidation reaction conditions and do not form explosive mixtures with oxygen. The inert gas preferably used comprises nitrogen or an inert gas obtained by combustion of a methane-air mixture.

Suitable solvents are any solvents which are not oxidized or are only slightly oxidized by hydrogen peroxide under the selected reaction conditions and dissolve in water in a quantity of greater than 10 wt. %. Preferred solvents are those which are unlimitedly miscible with water. Suitable solvents are alcohols, such as for example methanol, ethanol or tert.-butanol; glycols, such as for example ethylene glycol, 1,2-propanediol or 1,3-propanediol; cyclic ethers, such as for example tetrahydrofuran, dioxane or propene oxide; glycol ethers, such as for example ethylene glycol monomethyl ether, ethylene glycol monoethyl ether, ethylene glycol monobutyl ether or propylene glycol monomethyl ethers and ketones, such as for example acetone or 2-butanone. Methanol is particularly preferably used as the solvent. Absorption is performed at a total pressure in the range from 1 to 25 bar, preferably at the same pressure as the epoxidation reaction, at which the exit gas containing oxygen is obtained. Absorption may be performed at temperatures between the melting point of the solvent and 100° C., preferably in the range from 0 to 60° C.

In a particularly preferred embodiment of the present invention, the inert gas stream and exit gas stream are passed countercurrently to the solvent. An absorption unit which is suitable for this embodiment is in particular a column with an inert packing or inserts, wherein the exit gas stream loaded with olefin and olefin oxide and the inert gas stream are fed into the bottom of the column, the solvent is supplied to the top of the column, the exit gas stream is discharged at the top of the column and the solvent stream loaded with olefin and olefin oxide is drawn off from the bottom of the column.

The process according to the invention is suitable for the epoxidation of olefins having 2 to 6 carbon atoms. The epoxidation of propene to yield propene oxide is most highly preferred. The process according to the invention is thus illustrated below using the epoxidation of propene by way of example.

Figure 1:
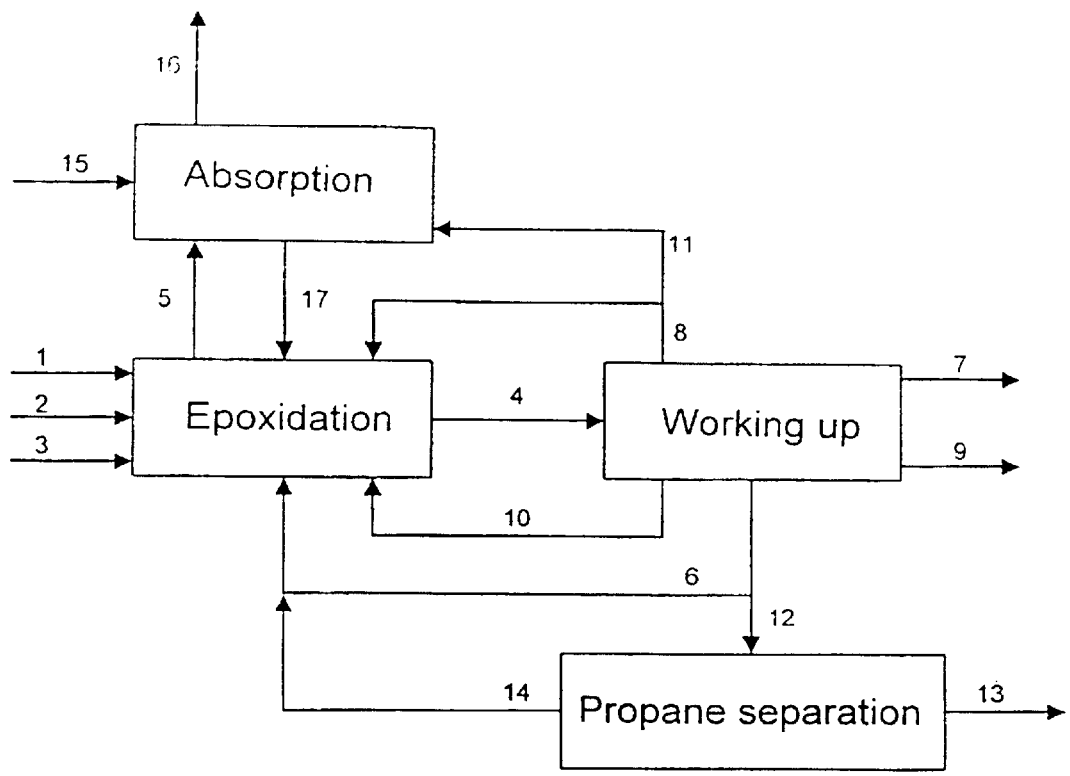
FIG. 1 shows one embodiment of the invention in which the absorption stage is incorporated into the epoxidation process in such a manner that the solvent stream loaded with propene and propene oxide during absorption is passed into the epoxidation reaction.
Figure 2:
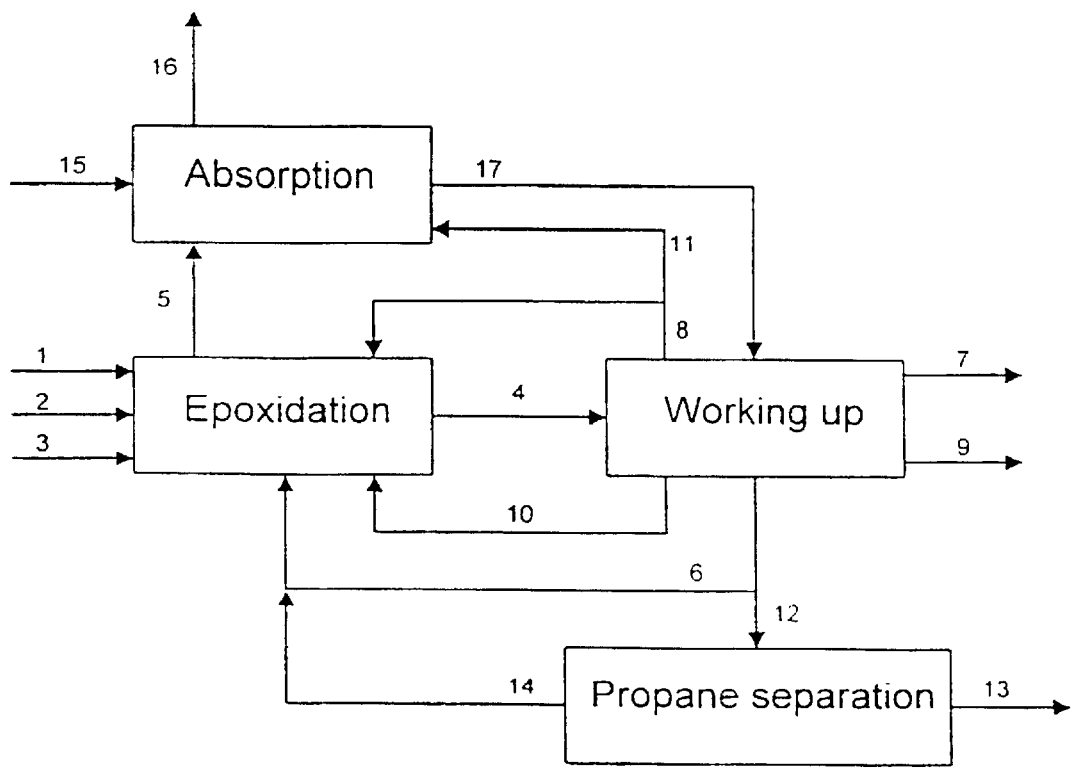
FIG. 2 shows an alternative embodiment of the present invention, in which the solvent stream loaded with propene, propane and propene oxide is passed not into the epoxidation stage but instead into the working up stage.

According to FIG. 1 or FIG. 2, propene is introduced into the epoxidation stage with stream 1, hydrogen peroxide with stream 2 and the solvent with stream 3, wherein stream 3 serves to make good any solvent losses in the process. A liquid reaction mixture leaves the epoxidation stage with stream 4 and an exit gas containing oxygen with stream 5. The liquid reaction mixture of stream 4 is separated during working up into stream 6, which substantially consists of propene and propane, stream 7, which substantially consists of propene oxide, stream 8, which substantially consists of the solvent, and stream 9, which substantially consists of water and high-boiling secondary products. When a suspended catalyst is used, working up also recovers the catalyst as stream 10, which is returned to the epoxidation, wherein a proportion of the catalyst or the entire catalyst is optionally subjected to a regeneration step beforehand. When a shaped catalyst is used which is retained in the epoxidation stage, stream 10 is not obtained. The recovered solvent from stream 8 is returned entirely or in part as stream 11 to the absorption stage. A substream 12 of the propene stream 6, which is returned to the epoxidation, is passed into the propane separation stage, from which a propane-enriched stream 13 is discharged, while the propane-depleted stream 14 is also passed into the epoxidation stage.

An inert gas stream 15 is also introduced into the absorption stage in addition to the exit gas stream 5 containing oxygen and the solvent stream 11. The inert gas leaves the absorption stage together with the oxygen from the epoxidation with the exit gas stream 16.

In the embodiment shown in FIG. 1, the solvent stream 17 loaded with propene, propane and propene oxide is returned to the epoxidation stage and the solvent stream 8 is divided such that preferably more than 30% and particularly preferably more than 80% are passed with stream 11 into the absorption stage.

In the embodiment shown in FIG. 2, the solvent stream 17 loaded with propene, propane and propene oxide is passed into the working up stage and the solvent stream 8 is divided such that preferably less than 50% and particularly preferably less than 30% are passed with stream 11 into the absorption stage.

Figure 3:
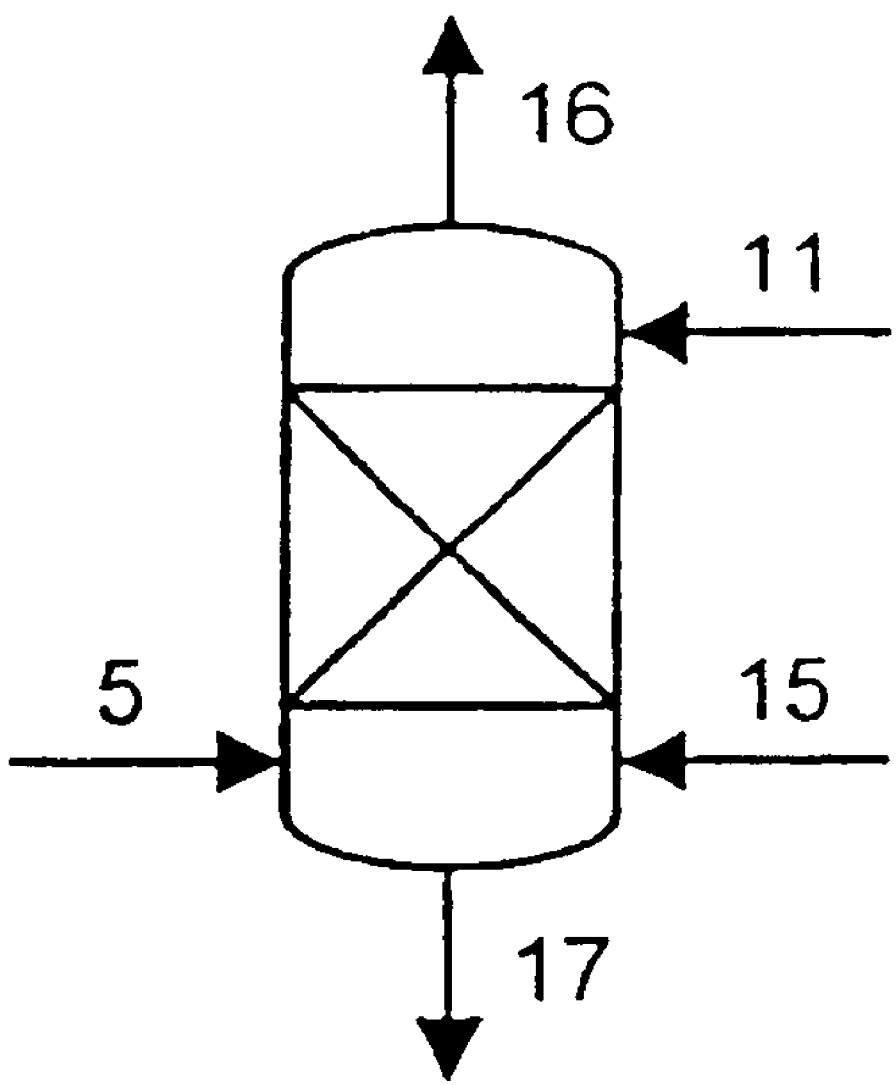
FIG. 3 shows an absorption unit suitable for the process according to the invention.

In the absorption stage, the exit gas stream 5 and the solvent stream 11 are passed countercurrently. The absorption stage preferably takes the form as shown in FIG. 3 of a column with an inert packing or inserts and is operated such that the gas streams 5 and 15 are fed into the bottom of the column and the exit gas stream 16 is drawn off from the top of the column, while the solvent is supplied with stream 11 into the top of the column and the loaded liquid stream 17 is withdrawn from the bottom of the column.

The quantity of inert gas is selected such that the exit gas stream 16, which, apart from inert gas, also contains oxygen together with small quantities of propene and solvent, is no longer of an ignitable composition.

In the epoxidation stage, stream 2 containing hydrogen peroxide may be mixed with a stream containing solvent (stream 8 and/or 17 in the embodiment according to FIG. 1 or stream 8 in the embodiment according to FIG. 2), before it is passed into the epoxidation reactor. Streams 1 and 6 containing propene may likewise be mixed before they are fed into the epoxidation reactor.

The process according to the invention has the advantage that only small quantities of propene and propene oxide are lost with the exit gas stream containing oxygen and that no additional auxiliary substances are required to recover the propene and propene oxide from the exit gas stream, as the solvent used for the absorption may be recirculated with the solvent used in the epoxidation reaction.

What is claimed is:

1. Process for the catalytic epoxidation of olefins in which in one reaction stage the olefin is reacted with aqueous hydrogen peroxide in an organic, water-miscible solvent in the presence of a titanium silicalite catalyst, wherein an exit gas stream (5) is obtained which contains olefin oxide, unreacted olefin and oxygen, characterized in that this exit gas stream (5) is brought into contact in an absorption unit with a solvent stream (11) consisting essentially of the same solvent as used in the reaction stage and a solvent stream (17) loaded with olefin and olefin oxide is drawn off from the absorption unit and an exit gas stream (16) containing oxygen is discharged.

2. Process according to claim 1, characterized in that an inert gas stream (15) is additionally introduced into the absorption unit, wherein the inert gas leaves the absorption unit together with the oxygen in the exit gas stream (16).

3. Process according to claim 2, characterized in that the quantity of inert gas introduced is selected as a function of the quantity and composition of the exit gas stream (5) leaving the reaction stage such that the exit gas stream (16) leaving the absorption unit is no longer of an ignitable composition.

4. Process according to claim 2, characterized in that the inert gas is selected from a gas which dissolves only slightly in the solvent used for epoxidation, does not react with hydrogen peroxide and olefin oxide under the epoxidation reaction conditions and does not form explosive mixtures with oxygen, preferably from nitrogen or an inert gas obtained by combustion of a methane-air mixture.

5. Process according to claim 2, characterized in that the inert gas stream (15) and the exit gas stream (5) are passed countercurrently to the solvent.

6. Process according to claim 1, characterized in that the absorption unit is a column with an inert packing or inserts and the gas streams (5, 15) are fed into the bottom of the column, the solvent is supplied to the top of the column as solvent stream (11), the exit gas stream (16) is discharged at the top of the column and the solvent stream (17) loaded with olefin and olefin oxide is drawn off from the bottom of the column.

7. Process according to claim 1, characterized in that the solvent stream (17) loaded with olefin and olefin oxide is either returned to the reaction stage or is passed to a working up stage downstream from the reaction stage.

8. Process according to claim 1, characterised in that the liquid product stream (4) from the reaction stage is worked up and the recovered solvent so obtained is returned in part to the absorption unit and in part to the reaction stage.

9. Process according to claim 1, characterised in that the olefin is an olefin having 2–6 carbon atoms, preferably propene.

10. Process according to claim 1, characterised in that the solvent is selected from among alcohols, glycols, cyclic ethers, glycol ethers and ketones and is preferably methanol.

* * * * *

UNITED STATES PATENT AND TRADEMARK OFFICE
CERTIFICATE OF CORRECTION

PATENT NO. : 6,624,319 B2  
DATED : September 23, 2003  
INVENTOR(S) : Hoffen, Willi et al.

Page 1 of 1

It is certified that error appears in the above-identified patent and that said Letters Patent is hereby corrected as shown below:

<u>Title page,</u>  
Item [56], References Cited, FOREIGN PATENT DOCUMENTS, please correct to read the following:

| | | | |
|---|---|---|---|
| -- | DE | 196 23 611 | 12/1997 |
| | DE | 197 23 950 | 12/1998 |
| | DE | 197 54 185 | 2/1999 |
| | DE | 198 35 907 | 2/2000 |
| | EP | 0 106 671 | 4/1984 |
| | EP | 0 100 118 | 2/1984 |
| | EP | 0 100 119 | 2/1984 |
| | EP | 0 757 045 | 2/1997 |
| | EP | 0 230 349 | 7/1987 |
| | EP | 0 230 949 | 8/1987 |
| | EP | 0 568 336 | 11/1993 |
| | EP | 0 568 337 | 11/1993 |
| | EP | 0 583 828 | 2/1994 |
| | EP | 0 645 473 | 3/1995 |
| | EP | 0 659 473 | 6/1995 |
| | EP | 0 712 852 | 5/1996 |
| | EP | 0 719 768 | 7/1996 |
| | EP | 0 795 537 | 9/1997 |
| | EP | 0 827 765 | 3/1998 |
| | EP | 0 930 308 | 7/1999 |
| | EP | 0 936 219 | 8/1999 |
| | EP | 1 066 711 | 12/1999 |
| | EP | 1 122 248 | 8/2001 |
| | EP | 1 138 387 | 10/2001 |
| | EP | 1 221 442 | 7/2002 |
| | JP | 2166636 | 6/1990 |
| | WO | WO 00/17178 | 3/2000 |
| | WO | WO 97/47613 | 12/1997 |
| | WO | WO 97/47614 | 12/1997 |
| | WO | WO 99/01445 | 1/1999 |
| | WO | WO 99/07690 | 2/1999 |
| | WO | WO 99/11639 | 3/1999 |
| | WO | WO 00/07695 | 2/2000 -- |

Signed and Sealed this

First Day of June, 2004

JON W. DUDAS  
*Acting Director of the United States Patent and Trademark Office*